United States Patent
Bruce et al.

(10) Patent No.: US 7,088,852 B1
(45) Date of Patent: Aug. 8, 2006

(54) THREE-DIMENSIONAL TOMOGRAPHY

(75) Inventors: Michael R. Bruce, Austin, TX (US); Victoria J Bruce, Austin, TX (US); Glen Gilfeather, Del Valle, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 734 days.

(21) Appl. No.: 09/833,247

(22) Filed: Apr. 11, 2001

(51) Int. Cl.
*G06K 9/00* (2006.01)

(52) U.S. Cl. .............................. 382/145; 438/6; 438/10

(58) Field of Classification Search ........ 382/141–151; 438/6–17
See application file for complete search history.

(56) References Cited

U.S. PATENT DOCUMENTS

| | | | | |
|---|---|---|---|---|
| 5,093,572 A | * | 3/1992 | Hosono | 250/310 |
| 5,196,353 A | * | 3/1993 | Sandhu et al. | 438/5 |
| 5,479,252 A | * | 12/1995 | Worster et al. | 356/237.5 |
| 5,514,957 A | * | 5/1996 | Tatebayashi | 324/309 |
| 5,561,293 A | * | 10/1996 | Peng et al. | 250/307 |
| 5,741,171 A | * | 4/1998 | Sarfaty et al. | 451/6 |
| 5,798,529 A | * | 8/1998 | Wagner | 250/492.21 |
| 5,844,416 A | * | 12/1998 | Campbell et al. | 324/750 |
| 5,972,725 A | * | 10/1999 | Wollesen et al. | 438/14 |
| 6,162,735 A | * | 12/2000 | Zimmermann et al. | 438/712 |
| 6,288,393 B1 | * | 9/2001 | Phaneuf et al. | 250/307 |
| 6,403,439 B1 | * | 6/2002 | Lee | 438/386 |
| 6,453,063 B1 | * | 9/2002 | Phaneuf et al. | 382/145 |
| 6,566,654 B1 | * | 5/2003 | Funatsu et al. | 250/310 |

* cited by examiner

*Primary Examiner*—Kanjibhai Patel
*Assistant Examiner*—Manav Seth
(74) *Attorney, Agent, or Firm*—Crawford Maunu PLLC (57) ABSTRACT

Defect analysis of a semiconductor die is enhanced in a manner that makes possible the viewing of spatial manifestations of the defect from virtually any angle. According to an example embodiment of the present invention, substrate is removed from a semiconductor die while simultaneously obtaining images of the portions of the die from which substrate is being removed. The images are taken at various points in the substrate removal process, recorded and combined together to form a three-dimensional image of selected portions of the die. The image is then used to view the selected portions, and the nature of one or more defects therein are analyzed.

13 Claims, 7 Drawing Sheets

THREE-DIMENSIONAL TOMOGRAPHY

FIELD OF THE INVENTION

The present invention relates generally to semiconductor devices and their fabrication and, more particularly, to testing and analysis of semiconductor dies.

BACKGROUND OF THE INVENTION

The semiconductor industry has recently experienced technological advances that have permitted dramatic increases in integrated circuit density and complexity, and equally dramatic decreases in power consumption and package sizes. Present semiconductor technology now permits single-die microprocessors with many millions of transistors, operating at speeds of hundreds of millions of instructions per second to be packaged in relatively small, air-cooled semiconductor device packages.

A by-product of such high-density and high functionality is an increased demand for products employing these microprocessors and devices for use in numerous applications. As the use of these devices has become more prevalent, the demand for faster operation and better reliability has increased. Such devices often require manufacturing processes that are highly complex and expensive.

As manufacturing processes for semiconductor devices and integrated circuits increase in difficulty, methods for testing and debugging these devices become increasingly important. Not only is it important to ensure that individual dies are functional, it is also important to ensure that batches of dies perform consistently. In addition, the ability to detect a defective manufacturing process early is helpful for reducing the number of defective devices manufactured.

The analysis of semiconductor dies often involves defect detection and identification. It is desirable to have the ability to determine the cause and location of defects in dies for various purposes, such as to improve upon the design or manufacture of the dies. However, analysis of semiconductor dies is inhibited by difficulties associated with locating and obtaining images of the defects. At times, locating a defect involves removing portions of the die to expose the defect. Accessing defects in the die can sometimes be destructive, and can inhibit the ability to adequately image a defect. In some instances, the defect itself may be obscured or removed before an image can be obtained. For these and other reasons, the detection, location and identification of defects has been challenging.

SUMMARY OF THE INVENTION

The present invention is directed to analyzing a semiconductor die in a manner that addresses the above-mentioned challenges. The present invention is exemplified in a number of implementations and applications, some of which are summarized below.

According to an example embodiment of the present invention, a three-dimensional image of an integrated circuit die is created and the die is analyzed therefrom. First, substrate is removed from a selected portion of the die, and a plurality of images of the selected portion are recorded as substrate is being removed. The plurality of images are combined and used to create a three-dimensional image of the selected portion of the die. The three-dimensional image is then used to analyze the selected portion, and improves the ability to detect, locate and identify defects in the die. The three-dimensional image is particularly useful, for example, for providing spatial manifestations of the selected portion, and the spatial manifestations can be used to locate a defect and show the shape thereof in applications including two-dimensional cross-sections and in three dimensions.

In another example embodiment of the present invention, a system is adapted for creating a three-dimensional image of an integrated circuit die. The system includes a substrate removal arrangement adapted to remove substrate from a selected portion of the die. An image recording arrangement is adapted to record sufficient images of the selected portion to make possible the generation of a three-dimensional image of the selected portion. An image creation arrangement is adapted to use the plurality of images recorded by the image recording arrangement to create a three-dimensional image of the selected portion of the die.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices, and has been found to be particularly suited for defect analysis in semiconductor dies. While the present invention is not necessarily limited to such devices, various aspects of the invention may be appreciated through a discussion of various examples using this context.

According to an example embodiment of the present invention, a semiconductor die having a defect, such as a defective electrical contact, a void, an open circuit or a short circuit is analyzed. Substrate is removed from a selected portion of the die having a suspected defect, and is removed in both horizontal and vertical directions as desired. The substrate removal uses commonly-available removal techniques, such as, for example, chemical-mechanical polishing (CMP), laser etching and focussed ion beam (FIB) etching. In addition, the extent of substrate removed is selected based on the application, and in some instances is global, wherein the entire die is thinned, in other instances is local wherein substrate is removed from a selected region in the die, and in other instances a combination of global and local thinning is used. While substrate is being removed from the potion of the die having a suspected defect, several images of the die are recorded. In one implementation, the images are recorded at a rate of 1 image per 1–5 seconds. In another implementation, images are recorded at intervals of substrate removal of between about 0.001 to 0.1 microns. The images are recorded using one or more imaging devices, such as an electron-beam device, a laser imaging device and/or a microscope. The substrate removal is continued until sufficient substrate has been removed to expose and image the defect. The recorded images are then used to create a three-dimensional image of the defect, which is analyzed therefrom.

In one particular example embodiment of the present invention, a dual FIB and electron beam (e-beam) tomography device is used to effect both the substrate removal and the capturing of images from a selected portion of a semiconductor die. The dual FIB/e-beam device is used to direct a FIB at a selected portion of substrate in the die. An etch gas selected to enhance the removal of substrate from the die is introduced to the die with the FIB. The dual FIB/e-beam device is used to direct an electron beam at the die, and the interaction of the electrons with the die is used to create an image of the die. For example, the e-beam is suitable for creating an image via scanning electron microscopy (SEM). The images taken are used to form a three-dimensional image of the die, and the three-dimensional images are viewed from one or more selected angles to determine the spatial manifestations of the defect.

In one particular implementation, the present invention is used in connection with defect analysis and identification methods used to identify a defective resistive interconnect. Resistive interconnects are often developed as a result of a void in conductive material used for the interconnect. For an example manner in which to identify a resistive interconnect, reference may be made to U.S. patent application Ser. No. 09/586,518, entitled "Resistivity Analysis" and filed on Jun. 2, 2000, which is incorporated herein by reference. In this example methodology, suspect circuitry in a semiconductor die is identified by using a state-changing operation of the circuitry to cause a failure due to the suspect circuitry. Using this state-changing operation one of the circuit paths that electrically changes in response to heat is identified; a particular circuit portion therein is identified as being defective because it is resistive. Once a resistive interconnect is identified, the interconnect is accessed and imaged in a manner not inconsistent with the various example embodiments described herein.

Figure 1:
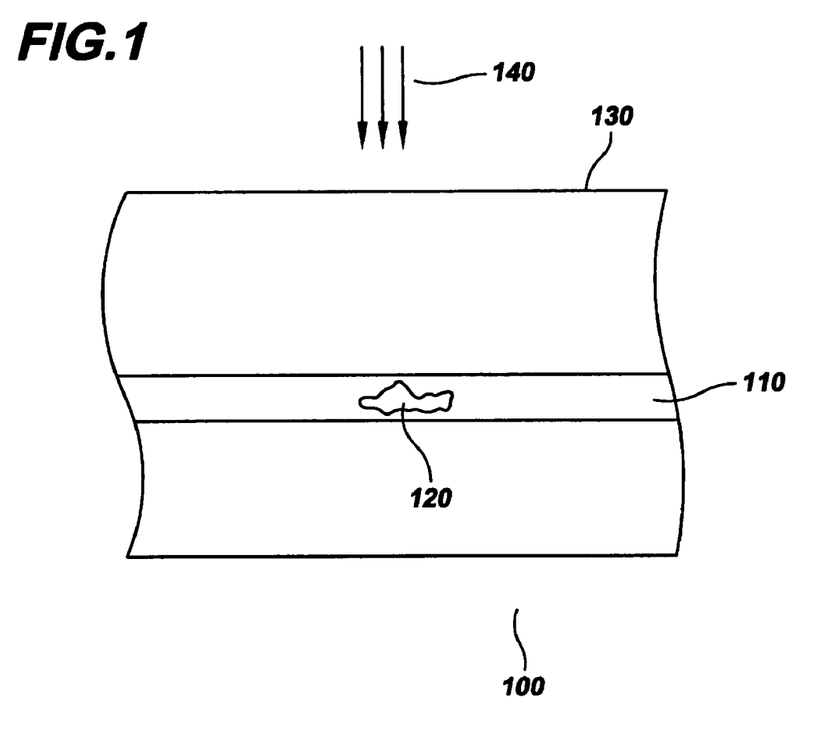
FIG. 1 is a semiconductor die undergoing analysis, according to an example embodiment of the present invention.
Figure 2:
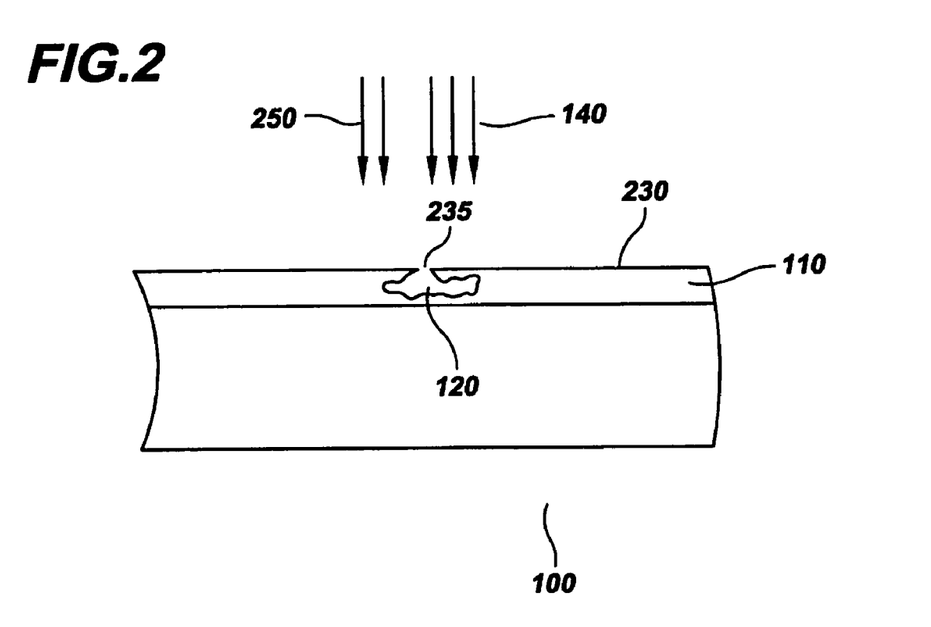
FIG. 2 is the semiconductor die of FIG. 1 undergoing further analysis, according to another example embodiment of the present invention.
Figure 3:
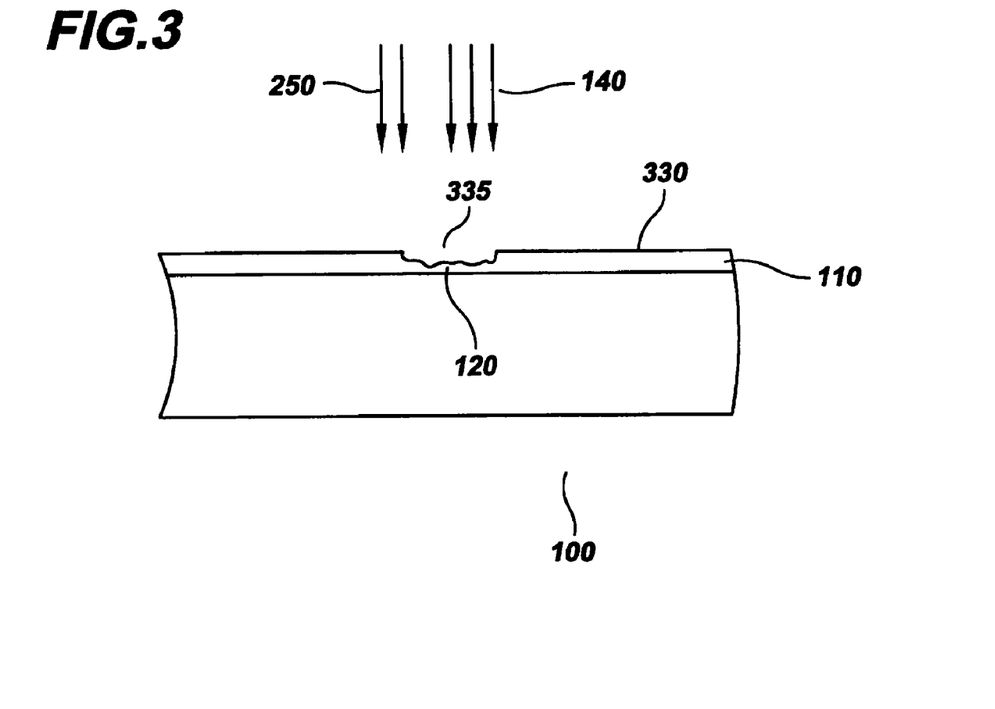
FIG. 3 is the semiconductor die of FIG. 2 undergoing further analysis, according to another example embodiment of the present invention.
Figure 4:
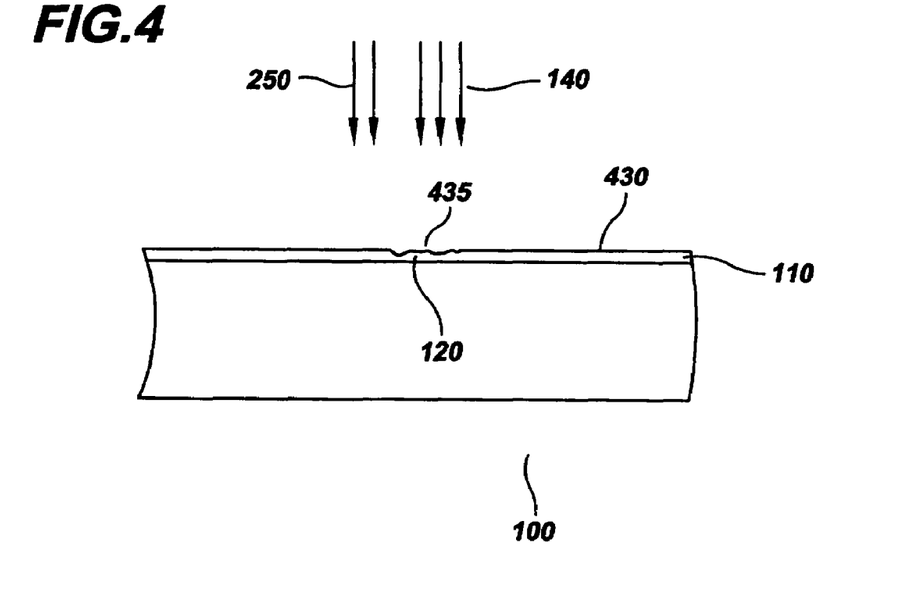
FIG. 4 is the semiconductor die of FIG. 3 undergoing further analysis, according to another example embodiment of the present invention.

The semiconductor die analysis of the present invention is applicable to a variety of types of semiconductor dies. FIGS. 1–4 show a portion 100 of one such semiconductor die undergoing cross-sectional analysis, according to an example embodiment of the present invention. A conductive interconnect 110 having a void defect 120 is analyzed. In FIG. 1, a FIB 140 is directed at a surface 130 of the die and substrate is removed therefrom. In FIG. 2, the FIB 140 has been used to remove substrate from the die 100 and expose surface 230. An e-beam 250 is directed at the die and used to obtain an image of the exposed surface 230, including the exposed portion 235 of the void defect 120. The image is recorded and the 140 is used to remove additional substrate, as shown in FIG. 3. Enough substrate is removed to expose surface 330 and a portion 335 of the void defect 120. An image of the portion 335 is taken with the e-beam 250 and recorded. In FIG. 4, additional substrate is removed with FIB 140 to expose surface 430 and a portion 435 of the void defect. Another image is taken of the die with the e-beam 250, the image including portion 435 of the void defect.

The images of the portions of the void defect 120 shown in FIGS. 2–4 are combined to form a three dimensional image of the defect. As the resolution of the image is desired to be increased, additional images are recorded in a similar manner at substrate removal levels between those shown in each of the figures. The images of the die are then stored and used to create a three-dimensional image for viewing the defect from any angle and at any depth into the defect. In one implementation, selected ones and/or portions of the stored images are used to create a three-dimensional image of a particular portion of the defect, such as a selected portion of a void. This is particularly useful for imaging only selected portions of a complex defect, such as a void having a variety of cavities extending in different directions. In another implementation, the three-dimensional image is created using all of the recorded images, and is subsequently edited to create an image of only a portion of the entire three-dimensional image, such as a portion representing a cross-section of the die.

Figure 5:
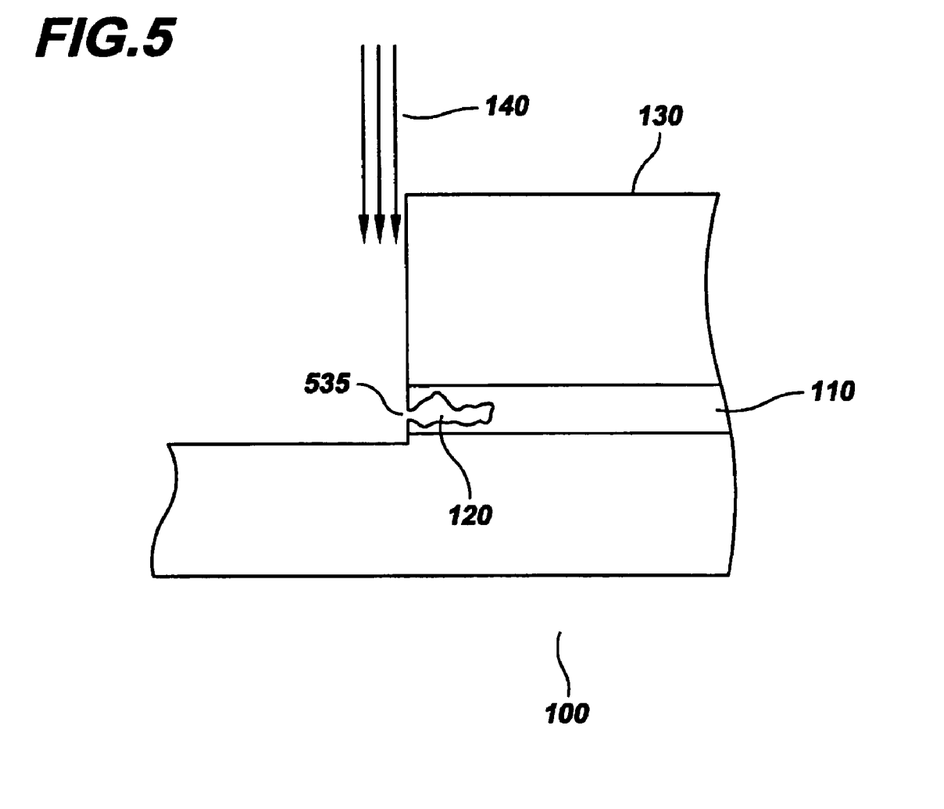
FIG. 5 is a semiconductor die undergoing analysis, according to another example embodiment of the present invention.
Figure 6:
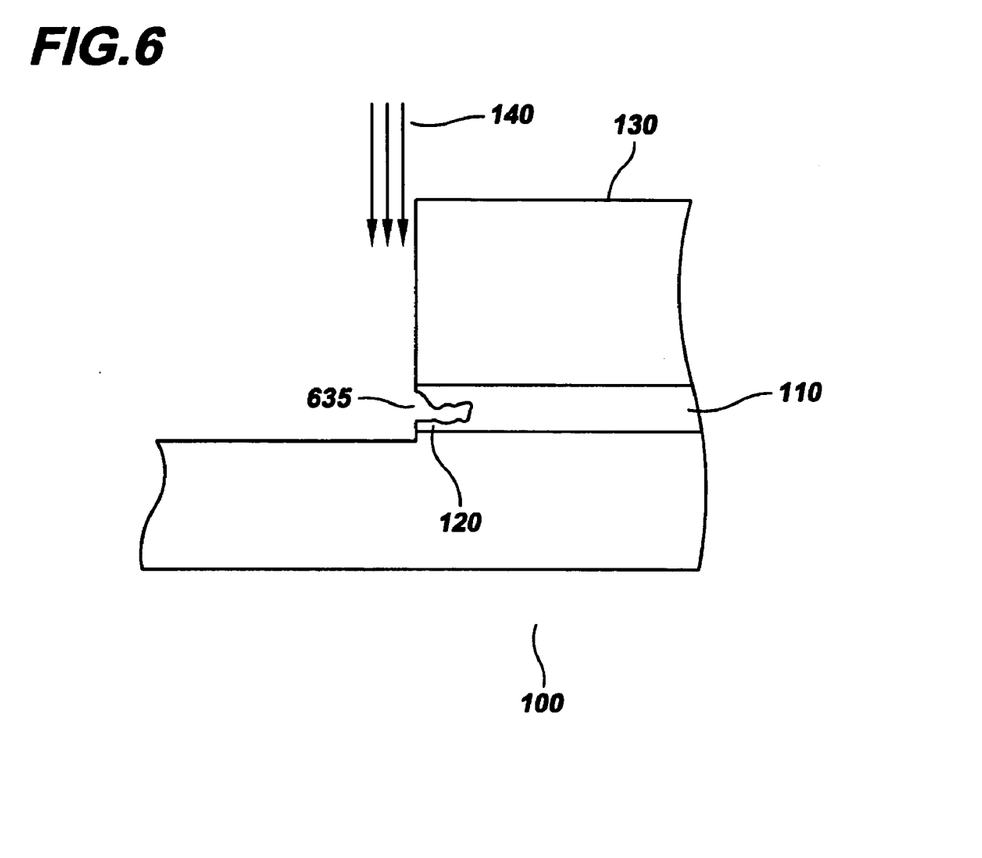
FIG. 6 is the semiconductor die of FIG. 5 undergoing further analysis, according to another example embodiment of the present invention.

FIGS. 5 and 6 show the die of FIGS. 1–4 undergoing a horizontal profiling of a defect, according to another example embodiment of the present invention. In FIG. 5, a FIB 140 is used to remove a portion of substrate from the die and to expose portion 535 of the defect 120. Images of the exposed portion are taken as the substrate is removed. Additional substrate is removed, as shown in FIG. 6, and an image of the exposed portion 635 is taken. The substrate removal and image acquisition is continued until the defect is profiled as desired. Several additional images of different stages of substrate removal are taken to improve the resolution of the imaged defect.

Figure 7:
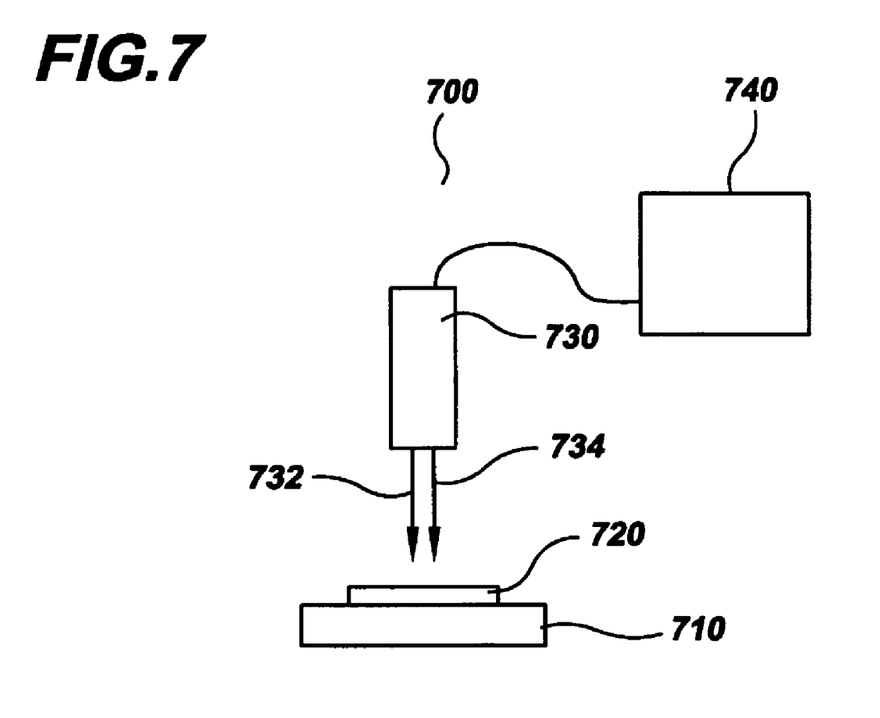
FIG. 7 is a system for analyzing a semiconductor die, according to another example embodiment of the present invention.

The analysis described herein is performed using selected equipment adapted for the particular implementation in which it is to be used. FIG. 7 is one such system 700 adapted to analyze a semiconductor die, according to an example embodiment of the present invention. A stage 710 is adapted to hold a semiconductor die 720 for analysis. A dual FIB/e-beam tomography device 730 is adapted to direct both a FIB 734 and an e-beam 732 at the die 720. The FIB 734 is used to remove substrate from the die and the e-beam 732 is used in combination with a microscope in the device 730 to obtain a SEM image of the die. The dual FIB/e-beam tomography device 730 is communicatively coupled to a controller 740. The controller 740 is adapted to control the e-beam and microscope to record sufficient SEM images of the die 720 as the FIB removes substrate to form a three-dimensional image of a defect in the die.

In one particular example embodiment of the present invention, the dual FIB/e-beam tomography device 730 includes a FEI XL830 available from FEI Company of 7451 NW Evergreen Parkway, Hillsboro, Oreg. 97124-5830. In one example implementation, the device 730 is modified by programming it to effect SEM that acquires sufficient images for semiconductor die tomography, such as described hereinabove. More specifically, the creation of three-dimensional images while the FIB is used to mill through a defect in the die is facilitated by the acquisition of images at one or more of the rates discussed herein. The controller 740 is adapted to use the SEM images to form a three-dimensional image of the die that can be displayed using conventional SEM display methods, making possible the viewing of spatial manifestations of a defect in the die from any view angle or any two dimensional cross sectional view.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a suspected defect in an integrated circuit die, the method comprising:
   using a state-changing operation of suspect circuitry having the suspected defect to cause a failure due to the suspect circuitry and therein, to facilitate confirmation that the suspected defect should be further analyzed;
   in response to confirmation that the suspected defect should be further analyzed, removing substrate from a selected portion of the die to expose the suspected defect;
   recording a plurality of images of the selected portion as substrate is being removed therefrom; and
   creating a three-dimensional image of the selected portion of the die with the plurality of images and analyzing the die therefrom.

2. The method of claim 1, wherein removing substrate includes cross-sectioning the die, and wherein the suspected defect is a resistive defect characterized by one of the following: defective electrical contact, void, open circuit, short circuit.

3. The method of claim 1, wherein removing substrate includes using a FIB.

4. The method of claim 1, wherein recording a plurality of images includes using a SEM.

5. The method of claim 1, wherein removing substrate includes using a FIB produced by a dual FIB/e-beam device, and wherein recording a plurality of images includes using the e-beam of the dual FIB/e-beam device to create a SEM image.

6. The method of claim 5, further comprising programming a controller adapted to control the dual FIB/e-beam device to effect the recording of a sufficient amount of SEM images to create a three-dimensional image of the selected portion.

7. The method of claim 1, wherein removing substrate from the selected portion includes exposing a defect in the die, and wherein creating a three-dimensional image includes creating a three-dimensional image of the defect.

8. The method of claim 1, wherein creating a three-dimensional image includes combining the plurality of images of the selected portion and creating a combined image therefrom.

9. The method of claim 1, further comprising using the three-dimensional image to detect a defect in the die.

10. The method of claim 9, wherein creating a three-dimensional image includes creating an image of the defect, further comprising using the image of the detected defect to analyze the defect.

11. The method of claim 1, wherein creating a three dimensional image includes using selected ones of the plurality of images of the selected portion to create a three dimensional image of less than the entire selected portion.

12. The method of claim 1, further comprising editing the three dimensional image to create an edited image of only a portion of the three-dimensional image.

13. The method of claim 12, wherein editing the three-dimensional image includes creating an image of a cross-section of the selected portion.

\* \* \* \* \*